United States Patent
Mulford

(10) Patent No.: US 7,300,424 B1
(45) Date of Patent: Nov. 27, 2007

(54) ASPIRATOR AND ASSOCIATED METHOD

(76) Inventor: Thomas B. Mulford, 25 Eastwood Rd., Asheville, NC (US) 28803

( * ) Notice: Subject to any disclaimer, the term of this patent is extended or adjusted under 35 U.S.C. 154(b) by 0 days.

(21) Appl. No.: 11/397,068

(22) Filed: Apr. 3, 2006

(51) Int. Cl.
*A61M 1/00* (2006.01)
*A61M 5/00* (2006.01)

(52) U.S. Cl. .............. 604/319; 604/321; 604/316; 604/212

(58) Field of Classification Search ......... 604/316, 604/317, 319, 321, 118, 19, 212, 37, 902
See application file for complete search history.

(56) References Cited

U.S. PATENT DOCUMENTS

| | | |
|---|---|---|
| 338,045 A | 3/1886 | Easton |
| 1,253,955 A | 1/1918 | Galligan |
| 2,511,469 A | 6/1950 | Hawks |
| 2,672,141 A | 3/1954 | Filger |
| 2,890,699 A | 6/1959 | Miller |
| 3,017,880 A | 1/1962 | Brook |
| 3,266,532 A | 8/1966 | Stewart |
| 3,387,610 A | 6/1968 | Richmond |
| 4,102,342 A | 7/1978 | Akiyama et al. |
| 4,317,525 A | 3/1982 | Schuessler et al. |
| 4,539,985 A | 9/1985 | Magrath |
| 4,643,719 A | 2/1987 | Garth et al. |
| 4,729,765 A | 3/1988 | Eckels et al. |
| 4,805,611 A | 2/1989 | Hodgkins |
| 4,828,546 A | 5/1989 | McNeil et al. |
| 4,915,691 A | 4/1990 | Jones et al. |
| 4,921,488 A * | 5/1990 | Maitz et al. ........... 604/153 |
| 4,998,915 A | 3/1991 | Hannah |
| 5,002,534 A | 3/1991 | Rosenblatt |
| 5,098,418 A | 3/1992 | Maitz et al. |
| 5,114,415 A | 5/1992 | Shedlock |
| 5,562,077 A | 10/1996 | Schultz |
| 5,713,914 A | 2/1998 | Lee |
| 6,290,667 B1 | 9/2001 | Cook |
| 6,958,050 B1 | 10/2005 | Choski et al. |
| 6,994,087 B1 * | 2/2006 | Smith ............ 128/207.16 |

* cited by examiner

*Primary Examiner*—Jacqueline F. Stephens
(74) *Attorney, Agent, or Firm*—Carter Schnedler & Monteith, P.A.

(57) ABSTRACT

An aspirator, including a bulb that defines first and second ports, a tube adjacent to the first port defined by the bulb, and means for helping to prevent aspirated material inside the bulb from exiting the bulb through the second port defined by the bulb.

15 Claims, 4 Drawing Sheets

ASPIRATOR AND ASSOCIATED METHOD

This is a nonprovisional United States patent application directed toward an aspirator and an associated method.

BACKGROUND OF THE INVENTION

Aspiration plays an important role in many medical procedures and environments, for instance during care of a newborn human baby immediately after birth. Although patient safety is the primary concern during aspiration, the safety of the operator of the aspirator is also important. Without proper operator safety measures during aspiration, the operator could be contaminated by germs, bacteria, viruses, and the like that are entrained in the mucus, saliva, blood, amniotic fluid, or other material being aspirated from the patient.

DETAILED DESCRIPTION

Figure 1:
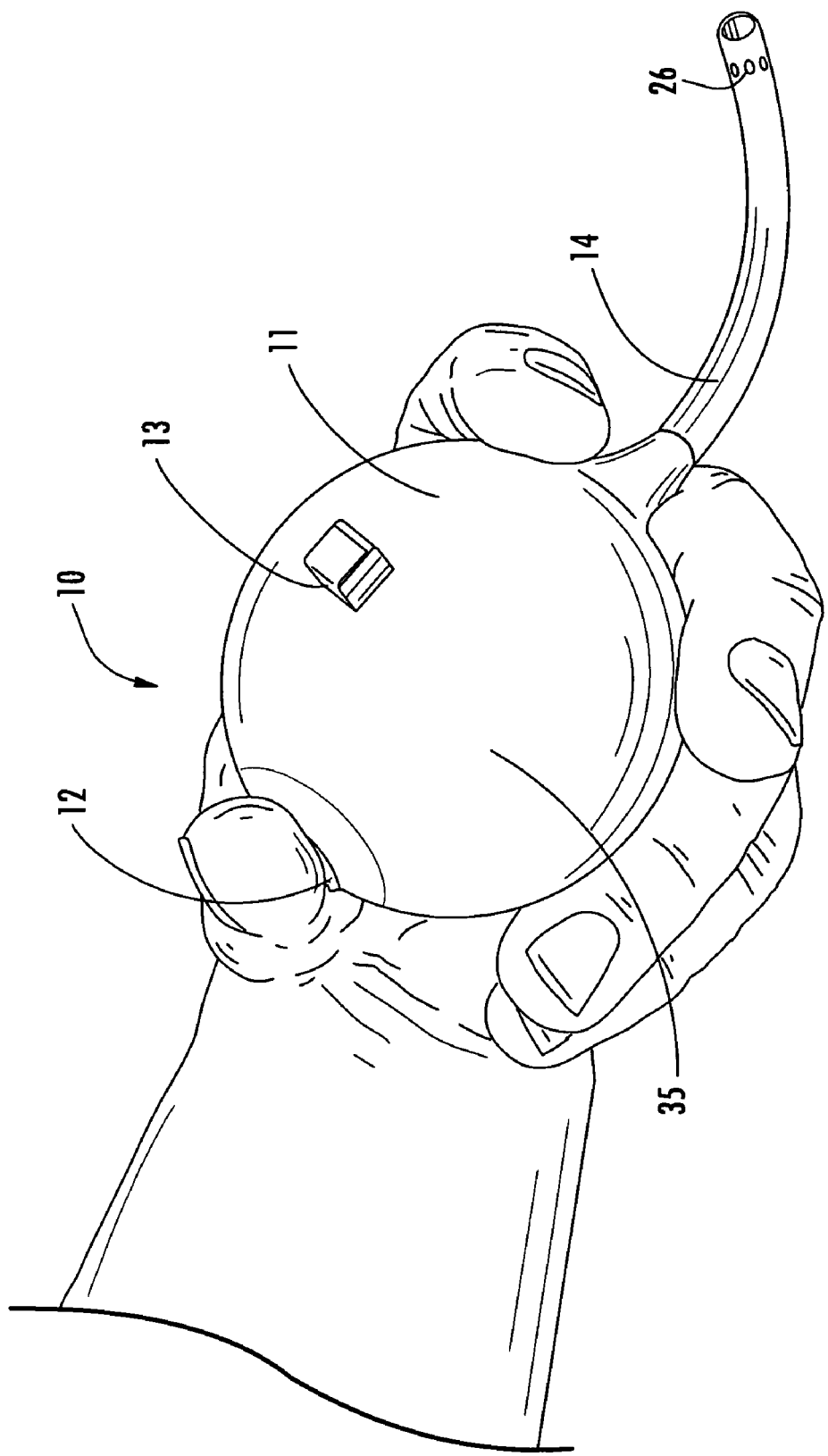
FIG. 1 is a perspective view of a pediatric embodiment of the invention positioned in a hand of an operator.
Figure 2:
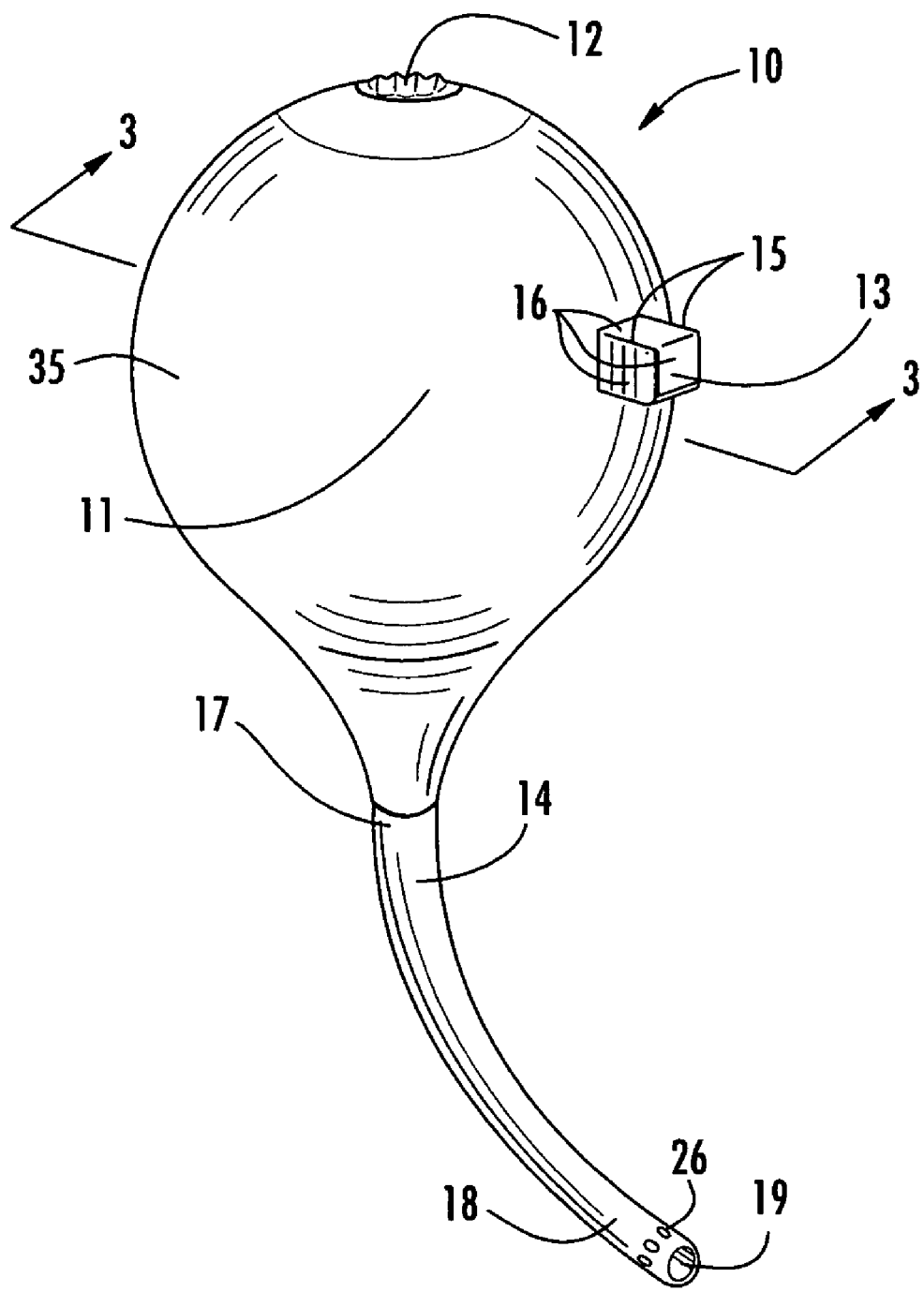
FIG. 2 is a perspective view of the embodiment of the invention shown in FIG. 1.

FIGS. 1 and 2 show an aspirator 10 according to an embodiment of the invention. The aspirator 10 is fabricated from any sterile, disposable, non-latex, single-use material that enables the functionality described herein or known and practiced by those of ordinary skill in the art, for instance, medical-grade plastic. The aspirator 10 includes a collapsible bulb 11 having an integral thumb grip 12, hood 13, and tube 14. The bulb 11 includes an interior wall 34 (FIG. 3) and an exterior wall 35. The aspirator 10 may be grasped in the manner shown in FIG. 1 or in any other manner that enables the functionality described herein or known and practiced by those of ordinary skill in the art. For instance, the thumb and fingers of the operator may be positioned along the periphery of the bulb 11 such that the thumb engages the thumb grip 12 and the tube 14 extends between either the pointer and middle fingers, the middle and ring fingers, or the ring and pinky fingers.

The thumb grip 12 is a plurality of ribs, ridges, or other raised structures that assist the operator with maintaining a secure grip on the aspirator 10. The hood 13 is a projection having a shape akin to that of an inverted scoop. Although the embodiment of the hood 13 illustrated in the drawings is provided with edges 15 defined by hood panels 16 intersecting at right angles, the hood 13 may alternatively have less defined edges or may be without edges altogether, i.e., strictly arcuate. In addition, although the hood 13 illustrated in the drawings is integral with the bulb 11, the hood 13 may alternatively be a separate structure that is fixedly or removably attached to the bulb 11. The tube 14 has a proximal end 17, a distal end 18, and an opening 19. The distal end 18 of the tube 14 defines perforations 26 in order to aspirate material from a broader area (not shown) than the area (not shown) proximal to the opening 19.

Figure 3:
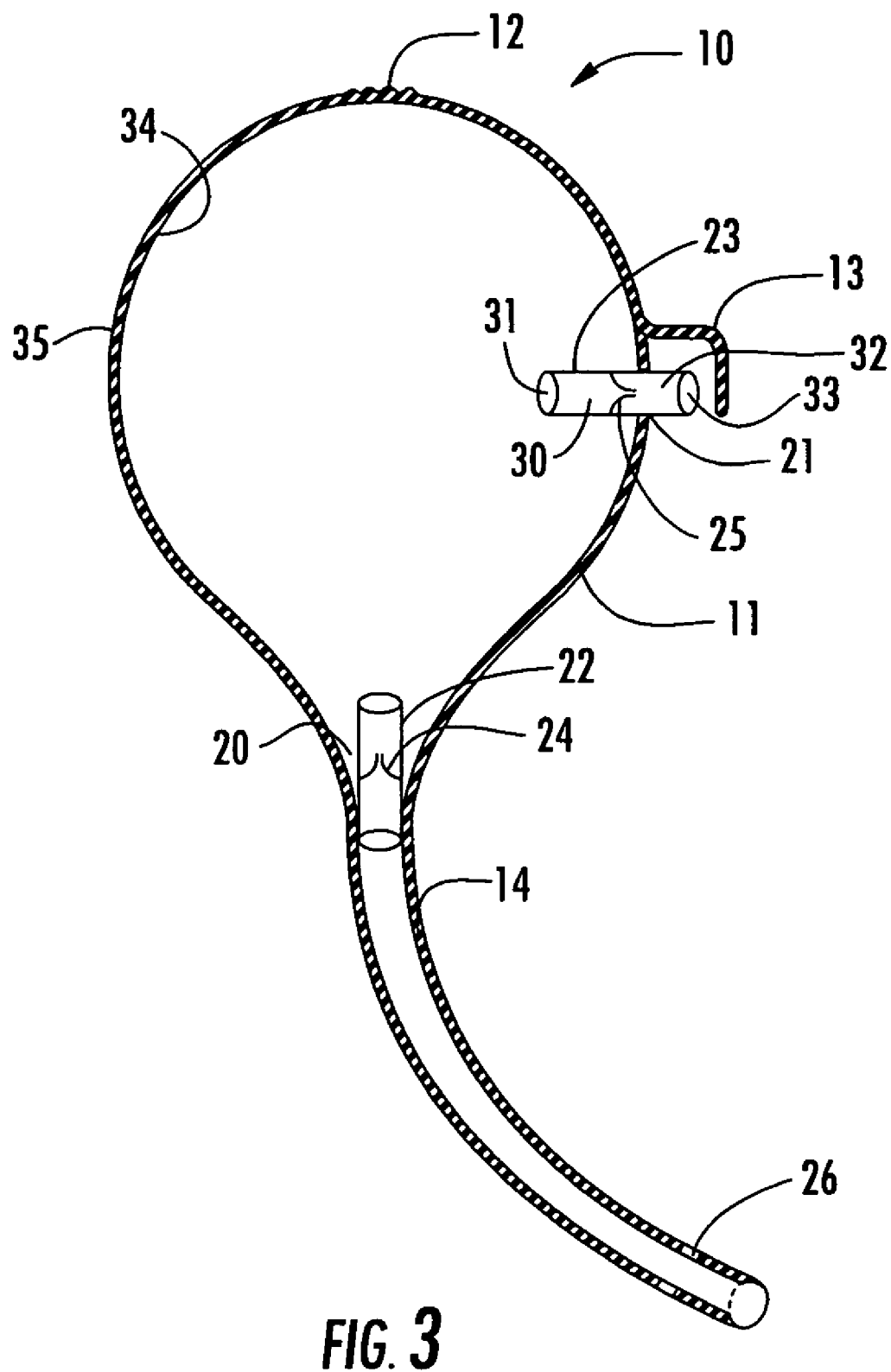
FIG. 3 is a cross-sectional view taken though line 3-3 of FIG. 2.

Turning now to FIG. 3, a cross-sectional view of the disclosed embodiment of the invention is shown. The bulb 11 defines first and second ports 20, 21. The first port 20 is substantially coaxial with the thumb grip 12, while the second port 21 is offset from the first port 20 by an angular distance of approximately 90 degrees. Each port 20, 21 carries a shunt 22, 23 that houses a valve 24, 25. The valves 24, 25 are one-way valves fabricated in accordance with the knowledge of those of ordinary skill in the art. The valve 24 in the first port 20 is designed to allow only entry into the bulb 11, while the valve 25 in the second port 21 is designed to allow only exit from the bulb 11. The shunts 22, 23 are installed in their respective ports 20, 21 in an airtight manner in order that all gaseous, liquid, and solid material entering and exiting the bulb 11 during use of the aspirator 10 must travel through at least one shunt 22, 23 and at least one valve 24, 25. The shunt 23 in the second port 21 includes an internal portion 30 that defines an internal opening 31 and an external portion 32 that defines an external opening 33.

A substantial majority of the gaseous, liquid, and solid material entering and exiting the bulb 11 (hereinafter "the aspirated material") during use of the aspirator 10 will enter and exit the bulb 11 through the first port 20 and the shunt 22 and valve 24 therein. The second port 21 primarily functions as an air vent to enhance the flow of such material through the first port 20. The internal portion 30 of the shunt 23 in the second port 21 is elongated such that the internal opening 31 defined by the shunt 23 is spaced apart from the interior wall 34 of the bulb 11 in order to help prevent aspirated material inside the bulb 11 from exiting the bulb 11 through the second port 21.

However, it is possible that some portion of the aspirated material will exit the bulb 11 through the second port 21. The orientation of the second port 21 at an approximately 90-degree angular separation from the thumb grip 12 and the first port 20, together with the hood 13, are provided to help prevent the aspirated material exiting the bulb 11 through the second port 21 from contaminating the operator of the aspirator 10. More specifically, because the head of the operator of the aspirator 10 is typically oriented above and behind the thumb grip 12 of the aspirator 10 during use of the aspirator 10, the 90-degree offset of the second port 21 relative to the thumb grip 12 reduces the likelihood that any aspirated material sprayed or otherwise ejected from the bulb 11 through the second port 21 will come into contact with the facial orifices of the operator (i.e., eyes, nose, mouth), through which contamination can easily occur. As a result, the hood 13 further reduces the likelihood of such contact by preventing aspirated material exiting the bulb 11 though the second port 21 from spraying or ejecting in an upward or outward direction toward the head of the operator or toward other areas of the operator's body that may cause ingestion of or be otherwise contaminated by the aspirated material. The hood 13 accomplishes this reduction by directing the aspirated material exiting the bulb 11 through the second port 21 generally downward and away from the operator.

During operation of the aspirator 10, the valves 24, 25 operate as follows. As the operator squeezes the bulb 11, the valve 24 in the first port 20 closes to prevent aspirated material from exiting the bulb 11 through the first port 20 while the valve 25 in the second port 21 opens to allow air to exit the bulb 11 through the second port 21; then when the operator releases the bulb 11, the valve 24 in the first port 20 opens to allow material being aspirated to flow into the bulb 11 while the valve 25 in the second port 21 closes to enhance suction as the bulb 11 returns to its resting shape.

The aspirator 10 of the invention may be provided in a variety of sizes in order to accommodate pediatric and adult patients. The embodiment of the invention shown in FIGS.

Figure 4:
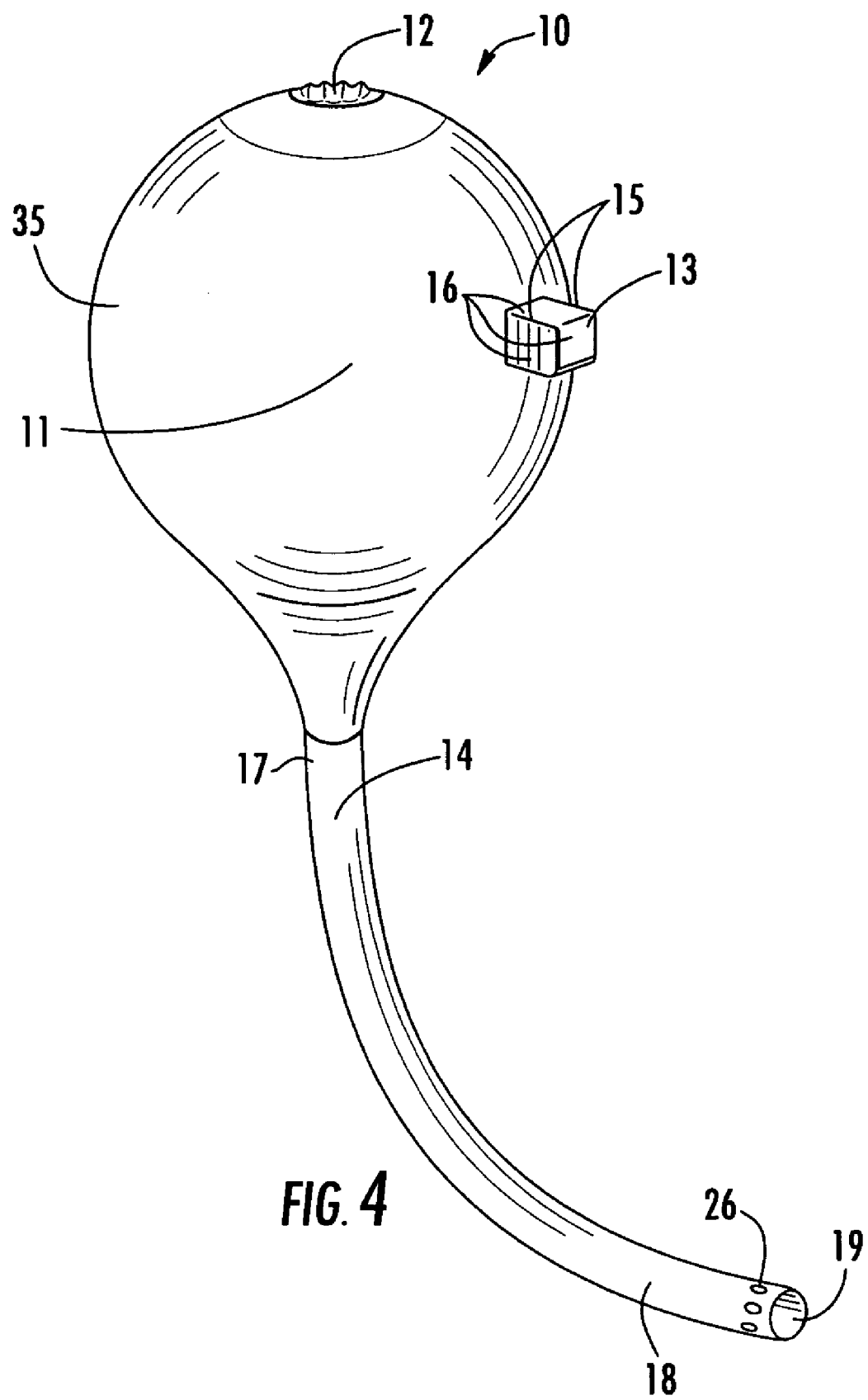
FIG. 4 is a perspective view of an adult embodiment of the invention.

1-3 is a pediatric aspirator, while the embodiment of the invention shown in FIG. 4 is an adult aspirator.

The aspirator 10 is used in the following manner. An operator grasps the bulb 11 in the manner described and illustrated herein and inserts the tube 14 into a predetermined orifice of a patient in order to impart or remove certain gaseous, liquid, and/or solid material from the orifice. The operator squeezes and releases the bulb 11 repeatedly as necessary to accomplish the desired aspiration. The aspirator 10 is then discarded.

An aspirator and associated is described herein. Various details of the invention may be changed without departing from its scope. Furthermore, the foregoing description of the invention and the best mode for practicing the invention are provided for the purpose of illustration only and not for the purpose of limitation—the invention being defined by the claims.

What is claimed is:

1. An aspirator, comprising:
a bulb defining first and second ports;
a tube adjacent to the first port;
a shunt in the second port, the shunt comprising an internal elongate portion within the bulb for helping to prevent aspirated material inside the bulb from exiting the bulb through the second port defined by the bulb; and
wherein the second port is offset approximately 90 degrees from the first port to help prevent aspirated material exiting the bulb through the second port from contaminating an operator of the aspirator.

2. An aspirator, comprising:
a bulb defining first and second ports and comprising an exterior wall, said first and second ports each carrying a valve;
a tube adjacent to said first port; and
a hood projecting from the exterior wall of the bulb, said hood being located adjacent to the second port but separated and spaced apart from the valve carried in the second port, wherein said hood helps to prevent aspirated material exiting the bulb through the second port from contaminating an operator of the aspirator.

3. An aspirator according to claim 2, wherein the hood forms an inverted scoop.

4. An aspirator according to claim 2, wherein the second port is offset approximately 90 degrees from the first port to further help to prevent aspirated material exiting the bulb through the second port from contaminating an operator of the aspirator.

5. An aspirator according to claim 2, wherein the valve carried in the second port is in a shunt.

6. An aspirator according to claim 2, wherein the hood is integrally formed with the bulb.

7. A method for aspirating, comprising:
providing an aspirator comprising a bulb, said bulb defining first and second ports, a tube adjacent to the first port defined by the bulb, and a shunt in the second port, the shunt comprising an internal elongate portion within the bulb for helping to prevent aspirated material inside the bulb from exiting the bulb through the second port defined by the bulb;
grasping the bulb of the aspirator;
inserting the tube of the aspirator into a predetermined orifice of a patient;
squeezing the bulb of the aspirator;
releasing the bulb of the aspirator;
repeating said squeezing and releasing steps as necessary to accomplish the desired aspiration; and
discarding the aspirator.

8. An method according to claim 7, wherein the first port defined by the bulb of the aspirator provided in said providing step and the shunt in the second port defined by the bulb of the aspirator provided in said providing step each carry a valve.

9. An method according to claim 7, wherein the second port defined by the bulb of the aspirator provided in said providing step is offset approximately 90 degrees from the first port defined by the bulb of the aspirator in order to help prevent aspirated material exiting the bulb through the second port from contaminating an operator of the aspirator.

10. A method according to claim 7, wherein the bulb of the aspirator provided in said providing step further comprises an interior wall and the internal elongate portion of the shunt defines an internal opening spaced apart from the interior wall of the bulb for further helping to prevent aspirated material inside the bulb from exiting the bulb through the second port defined by the bulb.

11. A method for aspirating, comprising:
providing an aspirator comprising
a bulb defining first and second ports and comprising an exterior wall, said first and second ports each carrying a valve;
a tube adjacent to said first port, and
a hood projecting from the exterior wall of the bulb, said hood being located adjacent to the second port but separated and spaced apart from the valve carried in the second port, wherein said hood helps to prevent aspirated material exiting the bulb through the second port from contaminating an operator of the aspirator;
grasping the bulb of the aspirator;
inserting the tube of the aspirator into an orifice of a patient;
squeezing the bulb of the aspirator;
releasing the bulb of the aspirator;
repeating said squeezing and releasing steps as necessary to accomplish the desired aspiration; and
discarding the aspirator.

12. A method according to claim 11, wherein the hood of the aspirator provided in said providing step forms an inverted scoop.

13. An method according to claim 11, wherein the second port defined by the bulb of the aspirator provided in said providing step is offset approximately 90 degrees from the first port defined by the bulb of the aspirator in order to further help to prevent aspirated material exiting the bulb through the second port from contaminating an operator of the aspirator.

14. A method according to claim 11, wherein the valve carried in the second port defined by the bulb of the aspirator provided in said providing step is in a shunt.

15. An method according to claim 11, wherein the hood of the aspirator provided in said providing step is integrally formed with the bulb of the aspirator.

* * * * *